United States Patent
Richardson et al.

(10) Patent No.: US 11,959,035 B2
(45) Date of Patent: Apr. 16, 2024

(54) FUELS AND PROCESSES FOR PRODUCING FUELS

(71) Applicant: KATAL ENERGY INC., Calgary (CA)

(72) Inventors: Aidan Richardson, Calgary (CA); Timothy Rose, Cranfield (GB); Craig Latimer, Calgary (CA); Mark Sajewycz, Toronto (CA)

(73) Assignee: Katal Energy Inc., Calgary (CA)

( * ) Notice: Subject to any disclaimer, the term of this patent is extended or adjusted under 35 U.S.C. 154(b) by 0 days.

(21) Appl. No.: 17/252,157

(22) PCT Filed: Jun. 14, 2019

(86) PCT No.: PCT/CA2019/050849
§ 371 (c)(1),
(2) Date: Dec. 14, 2020

(87) PCT Pub. No.: WO2019/237210
PCT Pub. Date: Dec. 19, 2019

(65) Prior Publication Data
US 2021/0246392 A1    Aug. 12, 2021

Related U.S. Application Data

(60) Provisional application No. 62/685,198, filed on Jun. 14, 2018.

(51) Int. Cl.
*C10L 1/32* (2006.01)
*C10L 1/12* (2006.01)
*G01N 33/28* (2006.01)

(52) U.S. Cl.
CPC ............... *C10L 1/328* (2013.01); *C10L 1/125* (2013.01); *G01N 33/287* (2013.01); *C10L 2200/0263* (2013.01); *C10L 2200/0295* (2013.01); *C10L 2200/0438* (2013.01); *C10L 2250/086* (2013.01); *C10L 2290/24* (2013.01)

(58) Field of Classification Search
CPC ...... C10L 1/328; C10L 1/125; C10L 2290/24; C10L 2200/0296; C10L 2200/0438; C10L 2250/086; C10L 2200/0263
See application file for complete search history.

(56) References Cited

U.S. PATENT DOCUMENTS

| 4,834,775 | A  | 5/1989  | Rodriguez et al. |
| 8,247,359 | B2 | 8/2012  | Martin |
| 2005/0262759 | A1* | 12/2005 | Tort ............ C10L 1/328 44/301 |
| 2016/0304798 | A1 | 10/2016 | Koh et al. |

FOREIGN PATENT DOCUMENTS

| WO | 2019036695 | 2/2019 |

* cited by examiner

*Primary Examiner* — Cephia D Toomer
(74) *Attorney, Agent, or Firm* — Smart & Biggar LP

(57) ABSTRACT

There is provided a process for producing a fuel comprising: sensing the sulphur content of a liquid hydrocarbonaceous material; admixing liquid aqueous material and the liquid hydrocarbonaceous material in a predetermined ratio, based upon the sensed sulphur content, such that a nanoemulsion is obtained; and converting the nanoemulsion into at least the fuel.

2 Claims, 1 Drawing Sheet

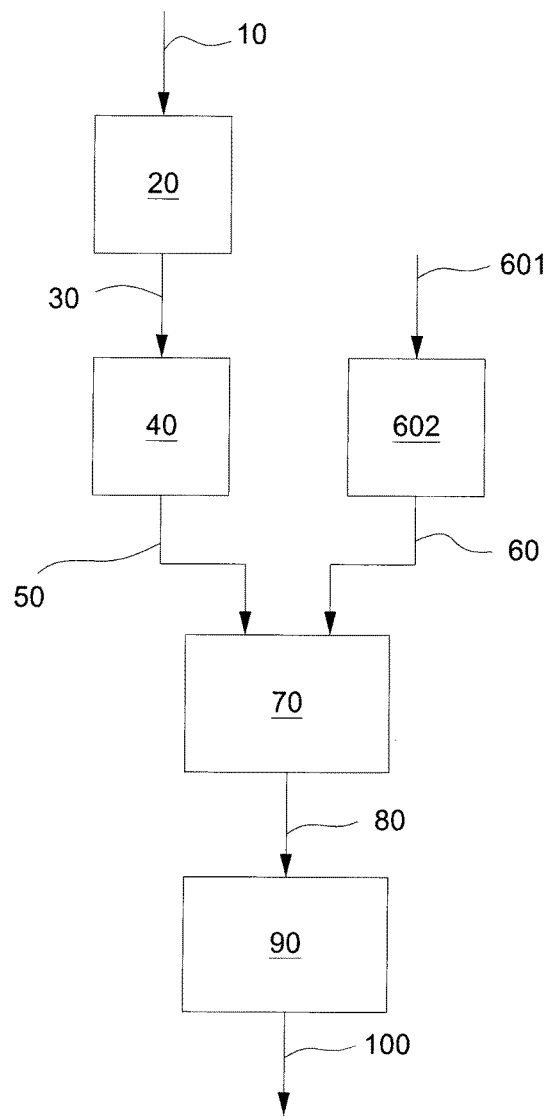

FUELS AND PROCESSES FOR PRODUCING FUELS

FIELD

The present disclosure relates to fuels and processes for producing fuels.

BACKGROUND

Environmental regulations have been promulgated that define the upper limit for sulphur in refinery products such as gasoline and diesel oil. Sulfur, in transportation fuels, increases $SO_x$ emissions. $SO_x$ is a significant pollutant, and detrimentally affects animal and plant life. It is desirable to reduce sulphur content in refinery products that are intended for combustion.

SUMMARY

In one aspect, there is provided a process for producing a fuel comprising: sensing the sulphur content of a liquid hydrocarbonaceous material, admixing liquid aqueous material and the liquid hydrocarbonaceous material in a predetermined ratio, based upon the sensed sulphur content, such that a nanoemulsion is obtained, and converting the nanoemulsion into at least the fuel.

BRIEF DESCRIPTION OF DRAWINGS

The embodiments will now be described with reference to the following accompanying drawings, in which:

FIG. 1 is a process flow diagram illustrating an embodiment of the present disclosure.

DETAILED DESCRIPTION

Referring to FIG. 1, there is provided a process for producing a fuel.

The fuel is derived from at least a liquid hydrocarbonaceous material 50. The liquid hydrocarbonaceous material includes hydrocarbonaceous matter.

The hydrocarbonaceous matter includes one or more hydrocarbon compounds, and typically includes a mixture of one or more hydrocarbon compounds. In some embodiments, for example, at least about 25 weight % of the liquid hydrocarbonaceous matter, based on the total weight of the liquid hydrocarbonaceous matter, is defined by one or more hydrocarbon compounds. In some embodiments, for example, at least about 50 weight % of the liquid hydrocarbonaceous matter, based on the total weight of the liquid hydrocarbonaceous matter, is defined by one or more hydrocarbon compounds. In some embodiments, for example, at least about 75 weight % of the liquid hydrocarbonaceous matter, based on the total weight of the liquid hydrocarbonaceous matter, is defined by one or more hydrocarbon compounds A "hydrocarbon compound" is an organic compound consisting primarily of hydrogen and carbon, and, in some instances, may also contain heteroatoms such as sulfur, nitrogen and oxygen.

In some embodiments, for example, each one of the one or more hydrocarbon compounds, independently has a boiling point within the range of from about 36.degrees Celsius. to about 1500.degrees Celsius.

In some embodiments, for example, the hydrocarbonaceous matter can also include impurities including sulfur and nitrogen compounds, nickel, vanadium, iron, and molybdenum. In this respect, in some of these embodiments, for example, the hydrocarbonaceous matter can include one or more of naturally occurring crude oil, synthetic crude oil (such as, for example, synthetic crude biodegraded oils), bitumen, oil sands, heavy oil, shale oil, or coal liquid.

In some embodiments, for example, the hydrocarbonaceous matter can include an upgraded hydrocarbonaceous product that is produced by upgrading a hydrocarbonaceous feedstock. The hydrocarbonaceous feedstock can include one or more of naturally occurring crude oil, synthetic crude oil (such as, for example, synthetic crude biodegraded oils), bitumen, oil sands, heavy oil, shale oil, or coal liquid. The hydrocarbonaceous feedstock can also include one or more partially upgraded hydrocarbonaceous products. Each one of the one or more partially upgraded hydrocarbonaceous products, independently, is derived from any one of naturally occurring crude oil, synthetic crude oil (such as, for example, synthetic crude biodegraded oils), bitumen, oil sands, heavy oil, shale oil, or coal liquid. Each one of the one or more partially upgraded hydrocarbonaceous products, independently, can be derived from a refinery process unit operation. Exemplary refinery process unit operations include atmospheric distillation, vacuum distillation, hydrotreating, hydroprocessing, fluid catalytic cracking, coking, visbreaking, solvent deasphalting and coal liquification. Each one of the one or more partially upgraded hydrocarbonaceous products, independently, can include vacuum gas oil, naphtha, fluid catalytic cracker gas oil, deasphalted oil, coker gas oil, and residuum.

As used herein, the term "upgrading", with respect to the hydrocarbonaceous feedstock, refers to a process that produces a hydrocarbonaceous product, derived from the hydrocarbonaceous feedstock, that, relative to the hydrocarbonaceous feedstock, is lighter, and/or has at least one of a higher API gravity, higher middle distillate yield, lower sulfur content, lower nitrogen content, or lower metal content, than does the hydrocarbonaceous feedstock.

In some embodiments, for example, the upgraded hydrocarbonaceous product can include one or more refinery products. Exemplary refinery products include gasoline, fuel oil, diesel oil, jet fuel, and kerosene. In this respect, in some embodiments, for example, the hydrocarbonaceous product is obtained by upgrading a hydrocarbonaceous feedstock via a refinery, and the process includes upgrading a hydrocarbonaceous feedstock 10 via a refinery 20 such that the hydrocarbonaceous product 30, and, therefore, the hydrocarbonaceous matter, is obtained.

In some embodiments, for example, the hydrocarbonaceous matter includes any one of marine diesel oil, marine gas oil, intermediate fuel oil, marine fuel oil, or heavy fuel oil. In some embodiments, for example, the hydrocarbonaceous matter includes any combination of marine diesel oil, marine gas oil, intermediate fuel oil, marine fuel oil, or heavy fuel oil.

In some embodiments, for example, the liquid hydrocarbonaceous material 50 can include conditioned hydrocarbonaceous matter that is produced by conditioning the hydrocarbonaceous matter. In this respect, the process includes conditioning the hydrocarbonaceous product 30 within a conditioning zone 40, with effect that the conditioned hydrocarbonaceous matter is obtained. In some embodiments, for example, the conditioning is with effect that the oxidation-reduction potential ("ORP") of the hydrocarbonaceous matter is increased. In some embodiments, for example, the conditioning is with effect that the surface tension of the hydrocarbonaceous matter (and, consequently, the interfacial tension of the hydrocarbonaceous matter, when mixed with an immiscible liquid) is reduced. In some embodiments, for example, the conditioning is effected by disposing the hydrocarbonaceous matter in close proximity to (such as, for example, in contact with) tiles that includes iron oxide associated with molecular cobalt (such as, for example, such as, for example, iron oxide on molecular cobalt stands) in a tank. In some embodiments, for example, the conditioning is effected by flowing the hydrocarbonaceous matter over the tiles.

The process includes admixing the liquid hydrocarbonaceous material 50 with liquid aqueous material 60, within a mixing zone 70, such that a fuel precursor 80 is obtained.

In some embodiments, for example, the liquid aqueous material 60 includes aqueous matter. In some embodiments, the aqueous matter is pure, or substantially pure, water. In some embodiments, for example, the aqueous matter comprises at least 90 weight % water, based on the total weight of the aqueous matter. In some embodiments, for example, the aqueous matter comprises at least 99 weight % water, based on the total weight of the aqueous matter.

In some embodiments, for example, the liquid aqueous material is aqueous matter 601 that has been conditioned. In this respect, the process includes conditioning the aqueous matter 601, within a conditioning zone 602, with effect that the liquid aqueous material 60 (i.e. conditioned aqueous matter) is obtained. In some embodiments, for example, the conditioning is with effect that the ORP of the liquid aqueous matter is decreased. In some embodiments, for example, the conditioning is effected by disposing the aqueous matter in close proximity (such as, for example, in contact with) to cerium oxide tiles, such as, for example, within a tank. In some embodiments, for example, the conditioning is effected by flowing the liquid aqueous matter over the tiles.

In some embodiments, for example, the ratio of weight of the liquid hydrocarbonaceous material 50 being admixed to the weight of liquid aqueous material 60 being admixed is based upon the sulphur content of the liquid hydrocarbonaceous material 50. In this respect, in some embodiments, for example, prior to the admixing, the sulphur content of the liquid hydrocarbonaceous material 50 is sensed by a sensor. In some embodiments, for example, the sensor is an in-line sensor. In some embodiments, for example, the sensor is a device that is external to the process, and the liquid hydrocarbonaceous material 50 is periodically sampled and analyzed by this external sensor.

In this respect, the liquid aqueous material 60 is admixed in a quantity sufficient to contribute to the production of a fuel which provides sufficient energy value while ameliorating the atmospheric effects of sulphur, when combusting the fuel, by effectively diluting sulphur concentration within the resultant fuel. With respect to marine gas oil, for example, it is desirable to reduce sulphur content to below 460 mg/kg. Advantageously, liquid hydrocarbonaceous material 50 with a higher sulphur content can be used with the processes discussed herein. In this respect, upgrading processes, employed in producing the liquid hydrocarbonaceous material from a hydrocarbonaceous feedstock 10, can be relaxed with respect to removing sulphur from the hydrocarbonaceous feedstock.

In some embodiments, for example, the fuel precursor is a nanoemulsion of liquid aqueous material in liquid hydrocarbonaceous material. In this respect, in some embodiments, for example, the admixing is effected by one or more shear nozzles, such as, for example, a plurality of shear nozzles in series. In some embodiments, for example, the admixing is effected by a nano-cavitation device. In some embodiments, for example, the liquid aqueous material is aerated with microbubbles prior to the admixing. The nanoemulsion includes a continuous hydrocarbonaceous phase and a discontinuous aqueous.

The fuel precursor is then converted to at least the fuel 100 within a reaction zone 90. In some embodiments, for example, the conversion includes an electrochemical conversion. In some embodiments, for example, the electrochemical conversion includes a partial redox reaction process. In some embodiments, for example, the reactive process is induced by a material initiator whose surface includes a mineral having electret properties. In some embodiments, for example, the In some embodiments, for example, the material initiator includes one or more active electret mineral compounds. An active electret mineral compound is a compound that is capable of initiating a partial redox reaction, via electrical interaction, of reactants that are moving in a direction that is perpendicular to the electrical field that is generated by the material initiator. In some embodiments, for example, each one of the one or more active electret mineral compounds independently, includes one or more lanthanides. Exemplary lanthanides include lanthanum, cerium, thorium, and neodymium. In some of these embodiments, for example, the material initiator is in the form of electrically active ceramic beads whose surface includes one or more active electret mineral compounds, and the fuel precursor is conducted through, successively, one or more material beds, each one of the one or more material beds, independently, being composed of a plurality of the electrically active ceramic beads described above.

The following illustrates how the processes described herein permit relaxation of sulphur reduction requirements for upgrading processes. Marine gas oil, having a density of 860 kg/m$^3$, a sulphur content of 826 mg/kg, and a net heat of combustion of 42.7 MJ/kg is supplied as the liquid hydrocarbonaceous material 50 and processed via the process illustrated in FIG. 1. The resultant fuel 100 has a density of 850 kg/m$^3$, a sulphur content of less than 460 mg/kg, and a net heat of combustion of 42.9 MJ/kg. Advantageously, the sulphur content is reduced, but not at the expense of the net heat of combustion (in fact, the net heat of combustion slightly increases).

The invention claimed is:

1. A process for producing a fuel comprising:
   sensing the sulphur content of a liquid hydrocarbonaceous material wherein:
   the sensing is effected with an in-line sensor; and
   admixing liquid aqueous material and the liquid hydrocarbonaceous material in a predetermined ratio, based upon the sensed sulphur content, such that a nanoemulsion is obtained.
2. The process as claimed in claim 1;
   wherein the liquid hydrocarbonaceous material is a refinery product.

* * * * *